(12) United States Patent
Slawson

(10) Patent No.: US 7,247,151 B2
(45) Date of Patent: Jul. 24, 2007

(54) INJECTOR WITH SHIELDED NEEDLE

(76) Inventor: Adam Slawson, 384 Queensbridge Road, Hackney, London (GB) E8 3AR ( * ) Notice: Subject to any disclaimer, the term of this patent is extended or adjusted under 35 U.S.C. 154(b) by 42 days.

(21) Appl. No.: 11/057,716

(22) Filed: Feb. 14, 2005

(65) Prior Publication Data
US 2005/0165362 A1 Jul. 28, 2005

Related U.S. Application Data

(63) Continuation-in-part of application No. 10/513,650, filed on Mar. 30, 2005, now abandoned.

(51) Int. Cl.
*A61M 5/32* (2006.01)
(52) U.S. Cl. ........................ 604/197; 604/110
(58) Field of Classification Search ............... 604/118, 604/121, 181, 182, 186, 187, 263, 192–199, 604/110–111
See application file for complete search history.

(56) References Cited

U.S. PATENT DOCUMENTS

| | | | |
|---|---|---|---|
| 3,090,383 A | | 5/1963 | Brooks |
| 3,337,031 A | | 8/1967 | Barr, Sr. et al. |
| 4,664,653 A | * | 5/1987 | Sagstetter et al. ........... 604/197 |
| 4,775,363 A | * | 10/1988 | Sandsdalen .................. 604/110 |
| 5,197,954 A | | 3/1993 | Cameron |
| 5,286,258 A | | 2/1994 | Haber et al. |
| 5,372,590 A | * | 12/1994 | Haber et al. ................. 604/192 |
| 5,376,080 A | | 12/1994 | Petrussa |
| 6,872,190 B1 | | 3/2005 | Denis et al. |

FOREIGN PATENT DOCUMENTS

| | | | |
|---|---|---|---|
| GB | 583611 | | 12/1946 |
| GB | 605522 | | 7/1948 |
| JP | 09314979 | | 3/1998 |
| WO | WO 99/39759 | * | 8/1999 |
| WO | WO 9939759 A1 | * | 8/1999 |
| WO | WO 01/54758 | * | 8/2001 |

OTHER PUBLICATIONS

International Search Report, PCT/EP2003/04856.

* cited by examiner

*Primary Examiner*—Nicholas Lucchesi
*Assistant Examiner*—Theodore J. Stigell
(74) *Attorney, Agent, or Firm*—Husch & Eppenberger LLC; Rebecca J. Brandau

(57) ABSTRACT

The present invention provides an injector device that can be used to inject a medicament. The injector device includes a body having a syringe cavity and incorporating a syringe. The syringe includes a barrel defining a reservoir for an injectable medicament and an injection needle is in communication with the reservoir such that the medicament content in the reservoir can be expelled from the reservoir via the needle. The syringe includes an internal piston which can be moved in an injecting direction along inside the barrel toward the needle to inject the medicament content through the needle. The syringe is slidably moveable within the syringe cavity in the body between a first configuration in which the needle has its point shielded, and a second configuration in which the needle is exposed for use for an injection to be administered, and back again.

14 Claims, 4 Drawing Sheets

INJECTOR WITH SHIELDED NEEDLE

CROSS-REFERENCE TO RELATED APPLICATIONS

Figure 1:
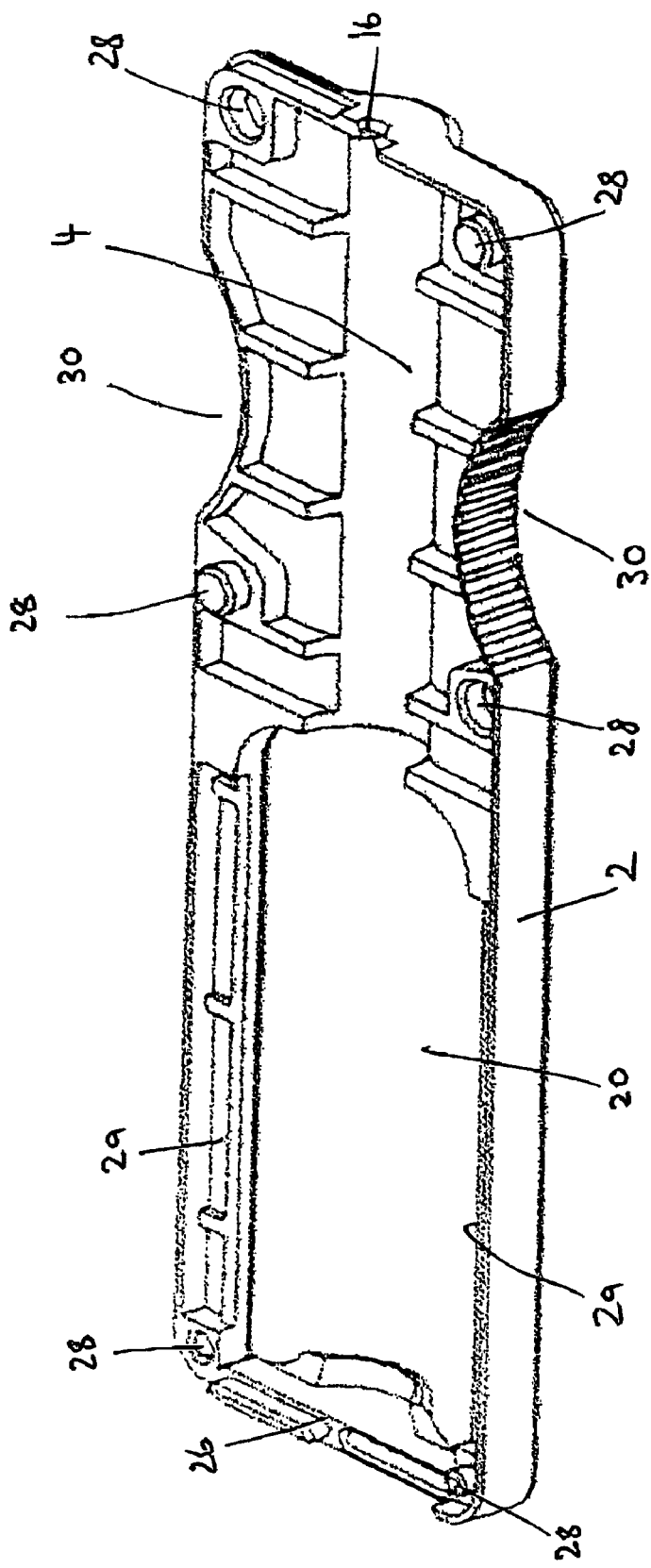

This application is a continuation-in-part of U.S. patent application Ser. No. 10/513,650, filed on Mar. 30, 2005 now abandoned, which claims priority of International Application No. PCT/EP03/04856, filed May 7, 2003, which claims priority of Great Britain Patent 0210631.8, filed May 9, 2002. The disclosures of the above applications are incorporated herein by reference in their entireties.

BACKGROUND OF THE INVENTION

Field of the Invention

This invention relates to injector devices.

Injector devices for the injection of a medicament into a patient's body, for example a hypodermic syringe in combination with an injection needle, are well known. Such syringes generally include a barrel defining a reservoir for the medicament, with an internal piston which can be moved along inside the barrel toward the needle, i.e. in the injecting direction, to eject the medicament content through the needle. The piston is normally engaged or engageable with a plunger shaft movable toward the syringe, to urge the piston in the injection direction.

It is common for users requiring administration of a medicament at an unpredictable time or in response to an emergency to carry with them an injector device loaded with a suitable medicament to inject themselves with in the event of need or an emergency. For example, diabetics may need to inject themselves with insulin. A particular emergency is anaphylaxis, a severe allergic reaction that affects the whole body, usually within minutes of exposure to an allergen but sometimes after a delay. The causes of anaphylaxis include certain foods, insect stings and certain drugs, and the remedy is an injection of adrenalin as soon as possible as an emergency measure. Other emergency situations may be those arising from a terrorist attack where a vaccine or medicinal countermeasure may need to be self-administered.

A problem with known injector devices is their lack of portability and their appearance, which can cause embarrassment to a user. Commonly used syringes of the usual type with a cylindrical barrel with an injection needle at one end and an internal piston driven by a plunger can also be fragile and of an awkward shape for convenient carriage by a user in for example a pocket or handbag etc.

It is an object of the present invention to provide an improved and alternative construction of an injector device which addresses the problems of such known injector devices.

According to this invention an injector device is provided including body having a syringe cavity and incorporating a syringe. The syringe has a barrel defining a reservoir for an injectable medicament; an injection needle in communication with the reservoir such that the medicament content in the reservoir can be expelled from the reservoir via the needle; and an internal piston which can be moved in an injecting direction along inside the barrel toward the needle to inject the medicament content through the needle. The needle has a point, and the syringe is slidably moveable within the syringe cavity in the body between a first configuration in which the needle has its point shielded, and a second configuration in which the needle is exposed for use for an injection to be administered.

The body is preferably, but not exclusively, substantially planar, and can be configured to accommodate a cylindrical syringe. The syringe cavity may for example be a generally cylindrical cavity and is preferably provided with guide means to guide the syringe as it slidably moves and to retain the syringe within the cavity.

Preferably, the body is substantially square or rectangular, i.e. two long sides and two short sides, optionally with rounded corners. For convenience, the body may have overall dimensions substantially of a standard "credit card" length and width, and there are certain advantages in making the body as thin as is practical to contain a suitable volume of medicament for delivery. In a body having such shape and dimensions it may be appropriate to have a syringe that is not cylindrical but rather of a flattened generally rectangular cross-section with its long sides parallel to the plane of the body, with a correspondingly sectioned barrel and internal piston.

The injector device preferably includes a plunger shaft for moving the internal piston in the injecting direction. Before the injector device is used to administer an injection and the syringe is in its first configuration, the plunger shaft is preferably connected to, or in abutment with, the internal piston. The plunger shaft may be fixedly connected to the internal piston, or may be connected to the internal piston by a severable link. This means that if the plunger shaft is fixedly connected to the internal piston then it can be used to move the internal piston back along the barrel of the syringe once the pre-loaded medicament has been injected. If the needle is placed in a fluid source then the movement of the internal piston in a direction opposite to the injecting direction will draw fluid into the reservoir and the injector device could then be reused to administer this fluid. This is generally not acceptable because it allows an injector device to be reused by the same or a different user to administer a fluid other than the preloaded medicament, such as illegal drugs and substances, with the associated health and hygiene risks. It is therefore preferred that the injector device cannot be reused. This can be achieved by making any connection between the plunger shaft and the internal piston severable so that the connection is broken if the plunger shaft tries to move the internal piston back along the barrel of the syringe after the medicament has been injected into the user. Alternatively, the plunger shaft and the internal piston can be formed separately and without any sort of connection between them. Movement of the internal piston in the injecting direction therefore relies on the contact between the end of the plunger shaft and the internal piston.

The needle will normally be provided sterile for use, and preferably when the syringe is in its first configuration, the needle, or at least its point, is shielded by providing a sterile envelope around the needle, or at least around its point. When the syringe is in its first configuration, the needle may be received within a cavity within the body, e.g. that in which the syringe slidably moves. The sterile envelope may take the form of a sterile cover that is provided around the needle, or at least around its point, or a sterile area or region such as the cavity in which the needle is located when it is in its first configuration. The injector device may also be provided for use sealed inside a sterile pack of foil or plastics material, for example.

The cavity may be closed by a rupturable cover and the movement of the syringe towards its second configuration may force the needle through the cover. Possible materials for the rupturable cover include foil, plastics and rubber materials.

By "shielded" herein is meant the needle being in such close proximity to the body, i.e. preferably received in a cavity as described above and preferably forming part of a sterile envelope, that it is in practice unlikely, preferably impossible for the needle to accidentally puncture the skin of the user or anyone else.

Further movement of the syringe in the injecting direction beyond its second configuration, and in the opposite direction beyond its first configuration may be prevented by stops. The stops may be formed as part of the body.

The injector device may include tamper-evident features such as a snap-off cap that is attached to the body via a frangible link and which must be removed before the user can gain access to the plunger shaft to move the syringe towards its second configuration. The other end of the body, i.e. the end through which the needle is exposed for use, may be covered by a cap. The cap can be made of a rubber or plastics material, for example, and can be releasably connected to the body in such a way that it must be removed before the syringe can be moved from its first configuration to its second configuration. The cap can be replaced back on the end of the body once the injector device has been used to inject the medicament.

Two or more of the injector devices may be provided linked together e.g. by a severable or frangible link, for example each injector device containing one unit of a multi-dose of the medicament. The injector device may incorporate two or more syringes, so that they may be used sequentially to administer sequential doses of the same or a different medicament.

The body and syringe may be made of conventional materials such as plastics materials. The syringe should be made of materials compatible with the medicament, and the needle will normally be metal.

The injector device can be operated by a user as follows. First of all, the user will apply an urging force to the plunger shaft in the injecting direction (i.e. toward the needle). The urging force is transmitted through the plunger shaft to the internal piston and/or the barrel and causes the syringe to move from its first configuration in which the needle has its point shielded, to its second configuration in which the needle is exposed for use for an injection to be administered. In practice, the urging force will cause the syringe to move without any relative movement between the internal piston and the barrel if the biasing force (see below) is significantly weaker than the resistive force of the medicament inside the barrel. If the resistive force is substantially the same as, or stronger than, the biasing force then there is a risk that the urging force will cause the internal piston to move along inside the barrel of the syringe while the syringe is in its first configuration, or in any event, before the syringe is in its second configuration when the needle is exposed for use. To prevent this from occurring, means are preferably provided to prevent any relative movement between the internal piston and the barrel of the syringe until the syringe is in its second configuration. For example, means such as a radially extending flange can be provided on the plunger shaft. The flange is initially in contact with the open end of the barrel and prevents the plunger shaft from moving relative to the barrel until the syringe reaches its second configuration. The point of the needle is then inserted into the user's skin and further application of an urging force to the plunger shaft causes the flange to break away from the plunger shaft and allows the internal piston to move in the injecting direction along inside the barrel toward the needle to inject the medicament content through the needle. Other means for achieving the same purpose can also be used in place of the flange. The means may be formed as part of the body instead of the plunger shaft.

The reservoir is preferably designed to contain sufficient medicament for a single injection and no more. When almost all of the medicament content has been injected, the internal piston will be in abutment with the end of the barrel to which the needle is connected. The retention of a small amount of medicament in the reservoir is a safety feature because if a bubble of air has accidentally found its way into the reservoir then as long as the injector device is used with its needle pointing downwardly the bubble of air will not be injected into the user. After the injection is complete and the urging force has been removed, it is preferred that the injector device is adapted such that the syringe is moved in a direction opposite to the injecting direction by a biasing force back towards its first configuration so that the point of the needle is once again shielded.

The syringe may be biased by a spring, an elastomeric bias, by compression of air as the syringe is moved to its second configuration or by any other suitable biasing means.

The biasing means may be located in the syringe cavity and may be adapted to apply the biasing force directly or indirectly to the end of the barrel that is connected to the needle.

The biasing means may also be adapted to bias the plunger shaft in a direction opposite to the injecting direction when the urging force has been removed. In this case, the plunger shaft (and/or the internal piston if it is connected to the plunger shaft) may be provided with engagement means for engaging with the barrel of the syringe to move it back towards its first configuration.

To prevent the injector device from being reused, the internal piston may also include a one-way mechanism that allows the internal piston to move in the injecting direction but which prevents movement in the opposite direction. Many such mechanisms are known, for example one-way barbs. Additionally or alternatively, the injector device may be provided with a mechanism such that when the syringe has been moved back towards its first configuration it may be locked in position.

The invention will now be described by way of example only with reference to the accompanying drawings which show:

FIG. 1 A perspective view of an injector device according to the present invention showing the body without a syringe, coil spring and plunger shaft.

Figure 2:
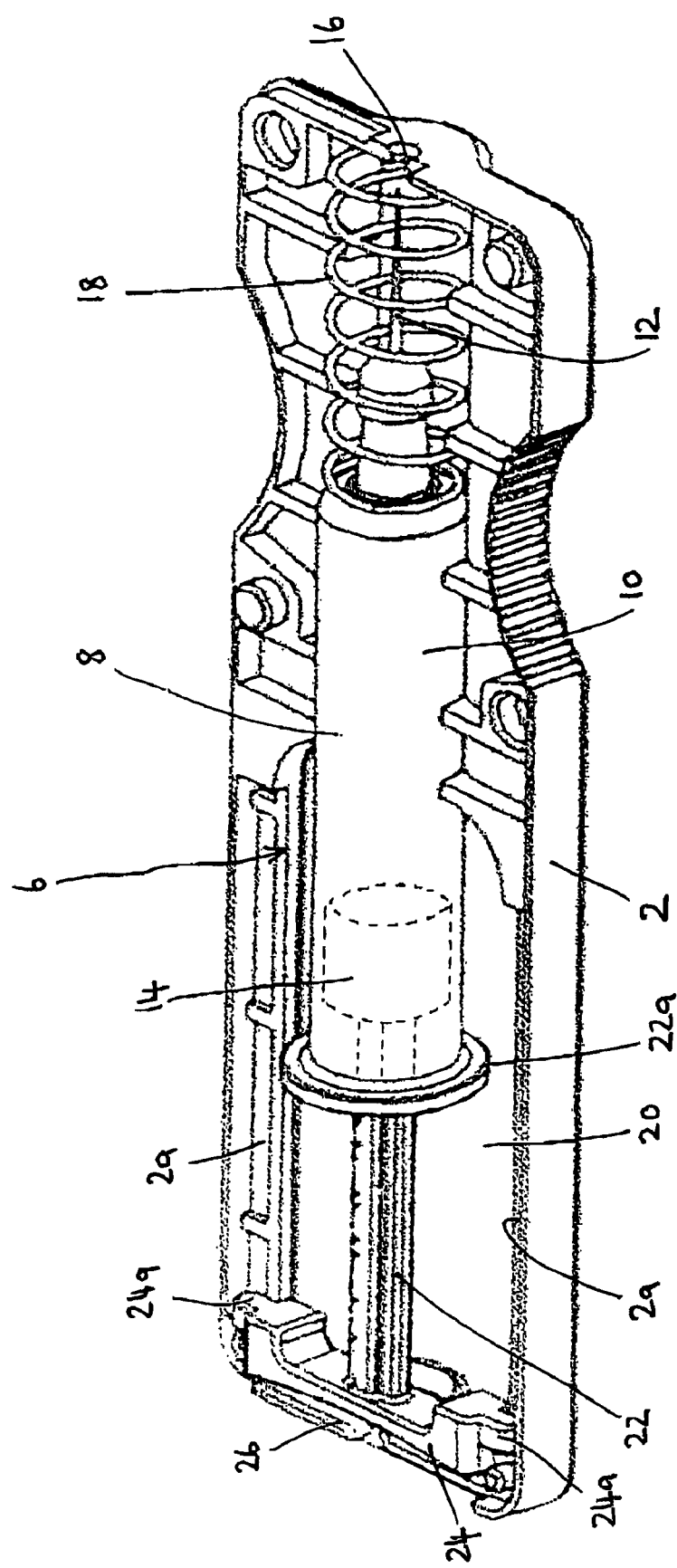

FIG. 2 A perspective view of the injector device of FIG. 1 with a syringe in its first configuration with the needle shielded.

Figure 3:
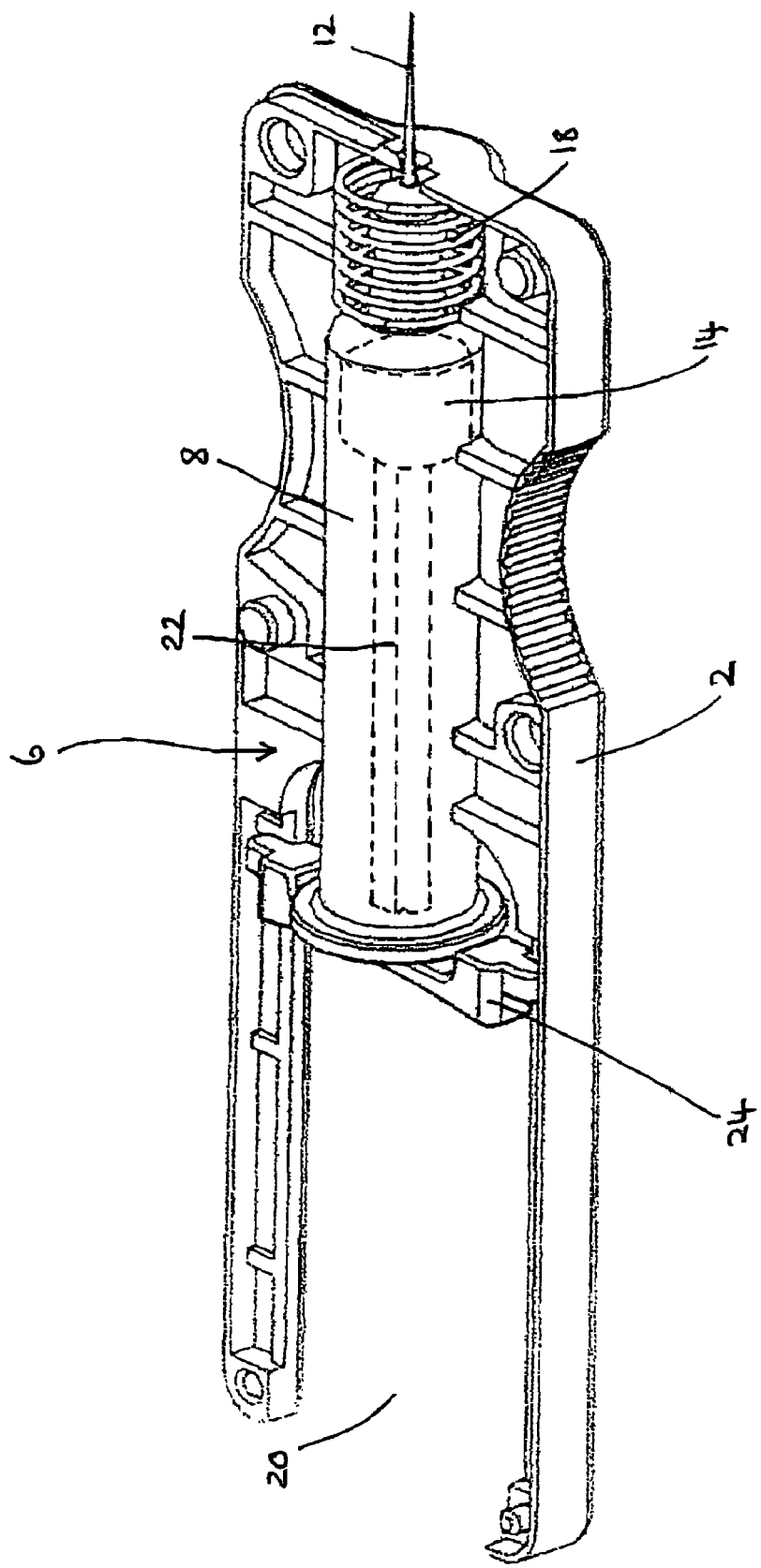

FIG. 3 A perspective view of the injector device of FIG. 1 with a syringe in its second configuration with the needle exposed for use.

Figure 4:
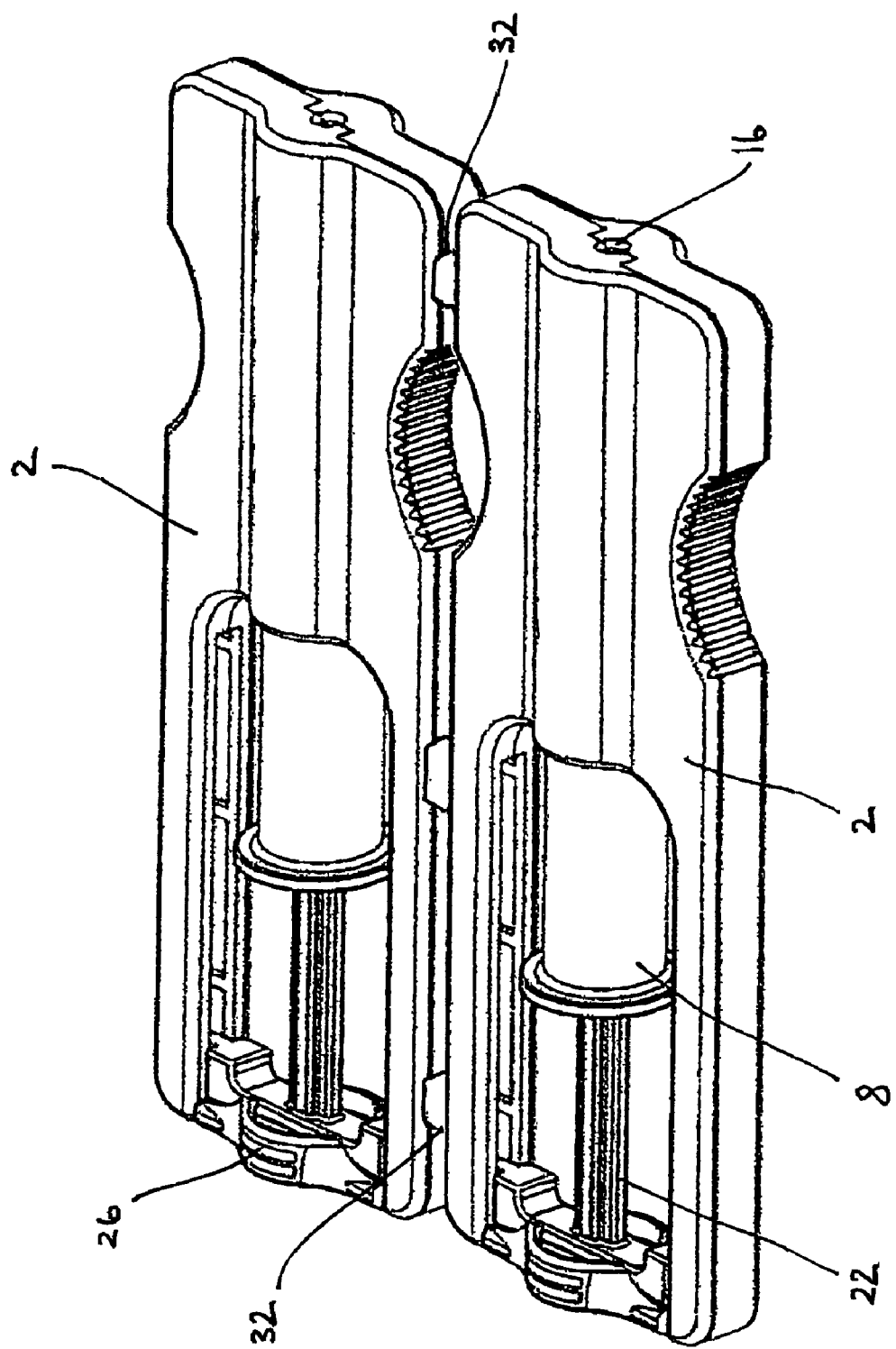

FIG. 4 A perspective view of a pair of injector devices joined together by a severable link.

DETAILED DESCRIPTION OF THE PREFERRED EMBODIMENTS

Referring to FIGS. 1 to 3, an injector device has a body 2, which is generally of a rectangular shape. The body is formed in two body halves, only one of which is shown in FIGS. 1 and 2, which are fixedly connected together during manufacture. It will also be readily appreciated that the body may be formed as a single unitary piece. The body incorporates a syringe cavity 4, which is generally cylindrical. A standard syringe 6 is located within the cavity 4 and includes a cylindrical barrel 8 defining a reservoir 10 for receiving an injectable medicament (not shown) and an injection needle 12 in communication with the reservoir such that the medicament content of the reservoir can be expelled from the reservoir through the needle. The syringe 6 includes an internal piston 14 that can be moved within the barrel 8 toward the needle 12 in a conventional manner. At one end of the cavity 4 there is a small opening 16 for the needle 12 that is closed by a rupturable cover (not shown) forming a sterile seal with the adjacent rim part of the opening. The other end of the cavity 4 is also provided with a sterile sliding seal e.g. an elastomer washer (not shown) between the body 2 and the outer surface of the barrel 8 so that the cavity is isolated from the ambient environment and the needle 12 remains sterile in a sterile envelope. The syringe 6 is slidably moveable within the syringe cavity 4 between a first configuration (as shown in FIG. 2) where the needle 12 is shielded inside the syringe cavity 4 and a second configuration (as shown in FIG. 3) where the syringe is advanced in an injecting direction such that the point of the needle is forced through the rupturable cover and the opening 16 so that an injection can be administered.

A coil spring 18 is located in the syringe cavity 4 and extends between a front part of the barrel 8 and an inner wall of the body 2. The needle 12 is received within the hollow centre of the coil spring 18 as shown.

The body 2 also includes a plunger cavity 20 in communication with the syringe cavity 4 for receiving a plunger shaft 22 and a rear part of the barrel 8. One end of the plunger shaft 22 is formed with a head part 24 that is operated by the user and includes projections 24a that are received in guide channels 2a that extend along the sides of the plunger cavity 20 and which are defined by the two body halves when secured together. The other end of the plunger shaft 22 includes a radially extending flange 22a which rests against the open end of the barrel 8 as shown in FIG. 2. The plunger cavity 20 is closed by a snap-off cap 26 that is joined to the rest of the body 2 by a frangible link. The other end of the plunger shaft 22 is received in the open end of the barrel 8 of the syringe and is initially in abutment with the internal piston 14. The end of the plunger shaft 22 that is received in the barrel 8 may include one or more radial fins (not shown) that contact the inner surface of the barrel to maintain the alignment of the plunger shaft as it slides within the barrel.

The body half shown in FIGS. 1 and 2 includes a number of projections and recesses 28 and these are received in corresponding recesses and projections provided in the other body half to align the two parts together. The two halves can be fixedly secured together during the manufacturing process by welding, gluing or the like. A pair of gripping areas, such as arcuate notches 30, for example, are provided on opposite sides of the body 2 to assist the user when the injector device 1 is being used to administer the medicament.

To use the injector device 1, the user must first remove the snap-off cap 26 that closes the plunger cavity 20 to expose the head part 24 of the plunger shaft 22. The snap-off cap 26 functions as a tamper evident feature and the user will know not to use the injector device 1 unless the cap is fully intact and is properly connected to the body 2 through the frangible link. The user then applies an urging force to the plunger shaft 22 by pressing on the head part 24 of the plunger shaft. This may be performed using the user's index finger while the user's thumb and middle finger are located in the notches 30 on either side of the body 2 to grip the injector device 1. The pressure on the head part 24 of the plunger shaft causes the syringe 6 to slide forward in the injecting direction such that the point of the needle 12 is forced through the rupturable cover (not shown) and the opening 16 and exposed for use. This movement of the syringe 6 within the syringe cavity 4 will compress the coil spring 18. As the syringe 6 moves forward in the injecting direction, the flange 22a prevents any relative movement between the plunger shaft 22 and the internal piston on the one hand, and the barrel 8 on the other hand. The flange 22a also transmits the urging force applied to the plunger shaft 22 directly to the barrel 8. Once the syringe is in its second configuration, the needle 12 is inserted into the user's skin and further pressure on the head part 24 of the plunger shaft 22 causes the flange 22a to break away from the rest of the plunger shaft 22 and allows the internal piston 14 to slide in the injecting direction within the barrel 8 and eject the medicament content of the reservoir into the user. The reservoir contains sufficient medicament for a single injection to be administered. Continuing pressure on the head part 24 of the plunger shaft 22 will eventually bring the internal piston 14 into abutment with the end of the barrel 8 to which the needle 12 is connected. At this point, no further movement of the syringe 6 or the internal piston 14 in the injecting direction is possible. The user then releases the pressure on the head part 24 of the plunger shaft 22 and the coil spring 18 provides a biasing force in a direction opposite to the injecting direction to move the syringe 6 back towards its first configuration where the needle 12 is once again shielded inside the syringe cavity 4. The plunger shaft 22 remains in abutment with the internal piston 14 and moves back with the syringe 6 under the biasing force of the spring 18. The internal piston 14 cannot be made to slide relative to the barrel 8 of the syringe 6 in a direction opposite to the injecting direction because there is no connection between the plunger shaft 22 and the internal piston. This prevents the injector device 1 from being reused. Alternatively, the internal piston 14 is provided with a different safety means (not shown) such as one-way barbs that allow the internal piston to move in the injecting direction but not in the opposite direction, or locking means to retain the syringe in its first configuration once the medicament has been injected. Once the needle is properly shielded, the used injector device 1 can be safely disposed of.

As shown in FIG. 4, a pair of injector devices can be connected together using frangible links 32. More than two such injector devices may be linked in such a manner. This enables plural injector devices each containing one unit of a multi-unit dose of the medicament, or one unit of two or more different medicaments, to be provided to the user in a convenient manner.

What is claimed is:
1. An injector device comprising:
   a body having a syringe cavity and incorporating a syringe, the syringe comprising:
   a barrel defining a reservoir for an injectable medicament;
   an injection needle in communication with the reservoir such that the medicament content in the reservoir can be expelled from the reservoir via the needle;
   an internal piston which can be moved longitudinally only in an injecting direction along inside the barrel toward the needle to inject the medicament content through the needle, the needle having a point, and the syringe being slidably moveable within the syringe cavity in the body between a first configuration in which the needle has its point shielded, and a second configuration in which the needle is exposed for use for an injection to be administered;

a plunger cavity;

guide channels that extend along the sides of the plunger cavity;

a plunger shaft located in the plunger cavity for moving the internal piston in the injecting direction, the plunger shaft having a head part with protrusions that are slidably received in the guide channels; and a snap-off cap that is attached to the body by a frangible link to close the plunger cavity and which must be removed to expose the head part of the plunger shaft prior to the injector device being used;

wherein the plunger shaft is slidably moveable within the plunger cavity by a manual urging force applied to the head part by a user thereto toward the syringe to urge the syringe toward the second configuration and to urge the internal piston in the injecting direction; and wherein the syringe is biased to be returned toward its first configuration after the manual urging force has been removed.

2. An injector device according to claim 1, wherein in its first configuration at least the point of the needle is shielded by providing a sterile envelope around at least the point of the needle.

3. An injector device according to claim 1, wherein in its first configuration the needle is received within the syringe cavity.

4. An injector device according to claim 3, wherein the syringe cavity is closed by a rupturable cover and the movement of the syringe towards its second configuration forces the needle through the rupturable cover.

5. An injector device according to claim 1, wherein the syringe is biased by a spring.

6. An injector device according to claim 5, wherein the spring is located in the syringe cavity.

7. An injector device according to claim 1, wherein the plunger shaft is fixedly connected to the internal piston.

8. An injector device according to claim 1, wherein the plunger shaft is connected to the internal piston by a severable link.

9. An injector device according to claim 1, wherein the plunger shaft and the internal piston are not connected to each other.

10. An injector device according to claim 1, further comprising a locking mechanism for locking the syringe in position once it has been moved back towards its first configuration.

11. An injector device according to claim 1, wherein the syringe cavity is closed by a cap that must be removed before the syringe can move from its first configuration to its second configuration.

12. An injector device according to claim 1, further comprising a structure for preventing relative axial movement between the internal piston and the barrel until the syringe is in its second configuration.

13. An injector device according to claim 1, wherein the injector device includes a one-way mechanism that allows the internal piston to move in the injecting direction, but which prevents movement in a direction opposite to the injecting direction; to thereby prevent reuse of the injector device.

14. An injector device comprising two or more devices according to claim 1, linked together by a severable link.

* * * * *